(12) United States Patent
Simpson et al.

(10) Patent No.: US 9,339,401 B2
(45) Date of Patent: May 17, 2016

(54) MEDICAL DEVICE UTILIZING A NICKEL-TITANIUM TERNARY ALLOY HAVING HIGH ELASTIC MODULUS

(71) Applicant: Abbott Laboratories, Abbott Park, IL (US)

(72) Inventors: John A. Simpson, Carlsbad, CA (US); John F. Boylan, Murrieta, CA (US)

(73) Assignee: ABBOTT LABORATORIES, Abbott Park, IL (US)

( * ) Notice: Subject to any disclaimer, the term of this patent is extended or adjusted under 35 U.S.C. 154(b) by 482 days.

(21) Appl. No.: 13/791,843

(22) Filed: Mar. 8, 2013

(65) Prior Publication Data

US 2014/0257451 A1 Sep. 11, 2014

(51) Int. Cl.
| | | |
|---|---|---|
| C22C 19/03 | (2006.01) |
| A61L 29/02 | (2006.01) |
| A61L 31/02 | (2006.01) |
| A61F 2/95 | (2013.01) |
| C22C 30/00 | (2006.01) |
| A61L 29/12 | (2006.01) |
| A61L 31/12 | (2006.01) |
| C22C 19/00 | (2006.01) |
| C22C 38/00 | (2006.01) |
| C22C 5/04 | (2006.01) |

(52) U.S. Cl.
CPC . *A61F 2/95* (2013.01); *A61L 29/02* (2013.01); *A61L 29/123* (2013.01); *A61L 31/022* (2013.01); *A61L 31/124* (2013.01); *C22C 19/007* (2013.01); *C22C 19/03* (2013.01); *C22C 30/00* (2013.01); *C22C 38/00* (2013.01); *A61L 2400/16* (2013.01); *C22C 5/04* (2013.01)

(58) Field of Classification Search
None
See application file for complete search history.

(56) References Cited

U.S. PATENT DOCUMENTS

| | | | | | |
|---|---|---|---|---|---|
| 4,505,767 | A | * | 3/1985 | Quin | 148/402 |
| 5,114,504 | A | * | 5/1992 | AbuJudom et al. | 148/402 |

(Continued)

FOREIGN PATENT DOCUMENTS

| | | |
|---|---|---|
| EP | 0873734 | 10/1998 |
| WO | WO 95/27092 | 10/1995 |

(Continued)

OTHER PUBLICATIONS

Ke-Bin Low et al., Eutectic Liquid Formation in the NiTi-Nb System: New Joining Method for Nitinol Point, Proceedings of the International Conference on Shape Memory and Superelastic Technologies (2008) pp. 829-836.

(Continued)

*Primary Examiner* — George Wyszomierski
(74) *Attorney, Agent, or Firm* — Workman Nydegger; John Kwok

(57) ABSTRACT

Medical devices that include a Ni—Ti ternary alloy and methods for their manufacture. The medical devices described herein include at least one part fabricated from the Ni—Ti ternary alloy. In the Ni—Ti alloys, the ternary alloying element is selected to be compatible with Ni—Ti. Example Ni—Ti ternary alloys include nickel (Ni), titanium (Ti), and one or more of tantalum (Ta), hafnium (Hf), vanadium (V), zirconium (Zr), scandium (Sc), or yttrium (Y). By virtue of their compatibility with Ni—Ti, additions of the ternary alloying element(s) may substitute for titanium in the Ni—Ti phase up to the solubility of the ternary element and the remainder can exist as a second phase whose mechanical properties resemble that of the pure ternary element and whose elastic modulus exceeds that of the Ni—Ti matrix.

16 Claims, 12 Drawing Sheets

(56) References Cited

U.S. PATENT DOCUMENTS

| | | | |
|---|---|---|---|
| 5,477,864 | A | 12/1995 | Davidson |
| 6,139,510 | A | 10/2000 | Palermo |
| 6,352,515 | B1 | 3/2002 | Anderson et al. |
| 6,428,634 | B1 | 8/2002 | Besselink et al. |
| 6,454,913 | B1 * | 9/2002 | Rasmussen et al. ..... 204/192.15 |
| 6,682,608 | B2 | 1/2004 | Abrams et al. |
| 7,128,758 | B2 * | 10/2006 | Cox .............................. 623/1.19 |
| 7,658,761 | B2 | 2/2010 | Yamauchi et al. |
| 7,717,864 | B1 * | 5/2010 | Grandfield et al. ........... 600/585 |
| 7,938,843 | B2 | 5/2011 | Boylan et al. |
| 8,128,579 | B2 | 3/2012 | Chen et al. |
| 8,211,164 | B2 | 7/2012 | Kramer-Brown et al. |
| 8,500,658 | B2 | 8/2013 | Boyle et al. |
| 2001/0049549 | A1 | 12/2001 | Boylan et al. |
| 2002/0082681 | A1 | 6/2002 | Boylan et al. |
| 2009/0068054 | A1 | 3/2009 | Ozawa et al. |
| 2010/0125329 | A1 | 5/2010 | Lin et al. |
| 2012/0039740 | A1 * | 2/2012 | Wojcik .......................... 420/441 |
| 2012/0041342 | A1 | 2/2012 | Purtzer |
| 2014/0255246 | A1 | 9/2014 | Simpson et al. |
| 2014/0257247 | A1 | 9/2014 | Simpson et al. |

FOREIGN PATENT DOCUMENTS

| | | |
|---|---|---|
| WO | WO 01/82830 | 11/2001 |
| WO | WO 02/36841 | 5/2002 |
| WO | WO 03/097147 | 11/2003 |
| WO | WO 2004/098458 | 11/2004 |

OTHER PUBLICATIONS

Piao, M. et al; Effects of Nb Addition on the Microstructure of Ti-Ni Alloys, Materials Transactions. JIM, Sendai, JP, vol. 33, No. 4, Jan. 1, 1992, pp. 337-345.

Guanjun, Y. et al; Study on the phase equilibria of the TiNiNb ternary system at 900 degrees C, Journal of Alloys and Compounds 297 (2000) pp. 226-230.

Yang, J.H. et al; Stress-Induced Transformation and Superelasticity in NiTiNb Alloys, Journal De Physique IV, Colloque C8, supplement au Journal de Physique III, vol. 5, Dec. 1995 pp. C8-771 to C8-776.

Gupta, K.P.; Phase Diagrams of Ternary Nickel Alloys, Part 2, Ternary Systems Containing CoNiX, MnNiX, MoNiX, NbNiX, NiTaX, NiTiX, NiVX, pp. 163-176, 1988.

Zhao, L.C. et al.; Transformation and Mechanical Behavior of a Ni47Ti44Nb9 Shape Memory Alloy, MRS International Meeting on Adv. Mets., vol. 9, 1989, pp. 171-176.

Prima, S.B. et al.; Investigation Methods and Properties of Powered Materials, Powder Metallurgy and Metal Ceramics, vol. 34, Nos. 3,4 1995, pp. 155-160.

Gong, C.W. et al.; Martensitic transformation of Ni50Ti45Ta5 shape memory alloy, Journal of Alloys and Compounds 419, 2006, pp. 61-65.

Ma, J.L. et al,; Microstructure and Transformation Behavior of Ni50Ti50-xTax Alloys, Materials Science Forum vols. 327-328, pp. 179-182, 2000.

Guanjun et al.; Constitutional Phases and Transformation Characteristics of a Ni47Ti44Ta9 Alloy, pp. 239-243.

Nickel Tantalum Titanium Ternary Alloy Phase Diagram (Based on 1991 Gupta K.P., ASM Alloy Phase Diagrams Center, 2007, pp. 1-3.

Lekston, Z. et al.; Phase Transformation in TiNiTa Shape Memory Alloy, Solid State Phenomena vol. 130 2007, pp. 147-150.

Schuessler, T. H.; Welding and Joining of TiNi Shape Memory Alloys: Engineering Aspects and Medical Applications, pp. 25-35, 1999.

Gong, C.W. et al.; Phase Transformation and second phases in ternary NiTiTa shape memory alloys, Materials Chemistry and Physics 96 (2006) pp. 183-187.

Cheng, Y. et al.; Surface modification of NiTi alloy with tantalum to improve its biocompatibility and radiopacity, J Mater Sci (2006) 41:pp. 4961-4964.

Simpson et al.; Cast Microstructure of a NiTiNb Shape Memory Alloy, Pract. Met. 23, 1986, pp. 357-361.

Xiao et al. Effects of Nb Content on Yield Strength of NiTiNb Alloys in Martensite State:, Chinese Journal of Aeronautics, 22, 2009, 658-662.

U.S. Appl. No. 13/791,851, Jan. 13, 2015, Office Action.
U.S. Appl. No. 13/791,851, Apr. 29, 2015, Notice of Allowance.
U.S. Appl. No. 13/791,860, Feb. 13, 2015, Office Action.
U.S. Appl. No. 13/791,860, May 21, 2015, Office Action.

* cited by examiner

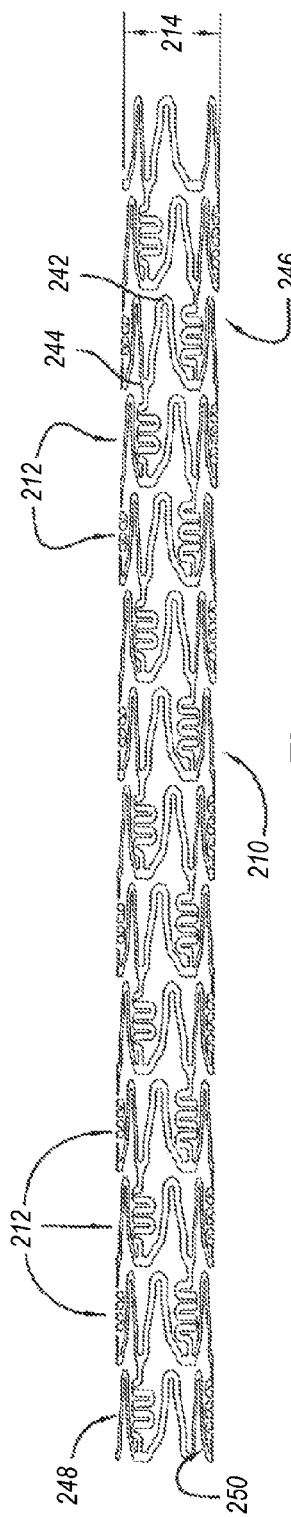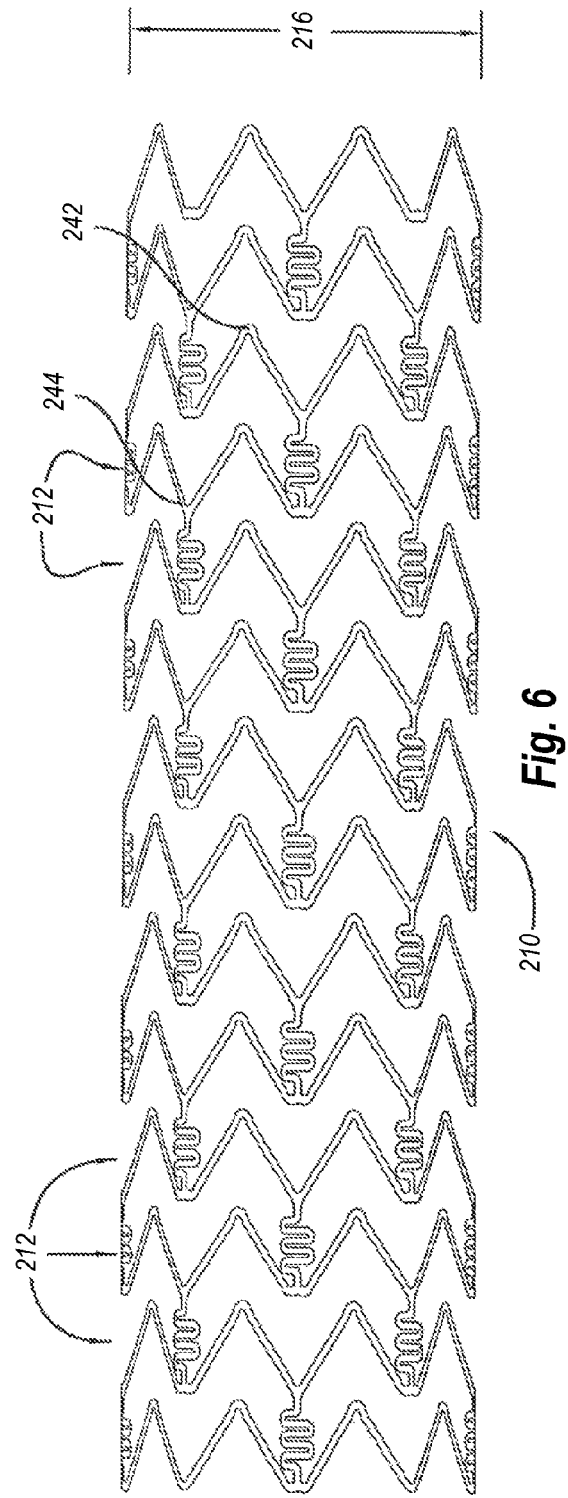
Fig. 5
Fig. 6

MEDICAL DEVICE UTILIZING A NICKEL-TITANIUM TERNARY ALLOY HAVING HIGH ELASTIC MODULUS

BACKGROUND

A wide variety of metal alloys are used to manufacture medical devices such as, but not limited to, guide wire devices, implantable vascular endoprostheses (e.g., stents), embolic protection filters, closure elements, and the like. Because of their high degree of biocompatibility and durability, nickel-titanium ("Ni—Ti") alloys are used for fabricating many medical devices.

For example, guide wires are used to guide a catheter for treatment of intravascular sites such as PTCA (Percutaneous Transluminal Coronary Angioplasty), or in examination such as cardio-angiography. For example, a guide wire used in the PTCA is inserted into the vicinity of a target angiostenosis portion together with a balloon catheter, and is operated to guide the distal end portion of the balloon catheter to the target angiostenosis portion.

A guide wire needs appropriate flexibility, pushability and torque transmission performance for transmitting an operational force from the proximal end portion to the distal end, and kink resistance (resistance against sharp bending). To meet such requirements, Ni—Ti alloys and high strength materials (e.g., stainless steel) have been used for forming a core member (wire body) of a guide wire.

Near equi-atomic binary nickel-titanium alloys are known to exhibit "pseudo-elastic" behavior when given certain cold working processes or cold working and heat treatment processes following hot working. Pseudo-elasticity can be further divided into two subcategories: "non-linear" pseudo-elasticity and "linear" pseudo-elasticity. "Non-linear" pseudo-elasticity is sometimes used by those in the industry synonymously with "superelasticity."

"Non-linear" pseudo-elastic Ni—Ti alloy exhibits upwards of 8% elastic strain (fully-recoverable deformation) by virtue of a reversible, isothermal stress-induced martensitic transformation. Non-linear pseudo-elasticity is known to occur due to a reversible phase transformation from austenite to martensite, the latter more precisely called "stress-induced martensite" (SIM). At room or body temperature and under minimal stress the material assumes a crystalline microstructure structure known as austenite. As the material is stressed, it remains in the austenite state until it reaches a threshold of applied stress (a.k.a. the "upper plateau stress"), beyond which the material begins to transform into a different crystal structure known as martensite. Upon removal of the applied stress, the martensite reverts back to the original austenite structure with an accompanying return to essentially zero strain (i.e., the original shape is restored).

A "linear" pseudo-elastic Ni—Ti alloy is processed by cold working the material (e.g., by permanently deforming the material such as by wire-drawing) without subsequent heat treatment (i.e., partial or full annealing). Residual permanent deformation, i.e., "cold work," tends to stabilize the martensitic structure so its reversion back to austenite is retarded or altogether blocked. With increasing levels of permanent deformation, the otherwise austenitic material becomes fully martensitic at room and body temperature, and further permanent deformation serves to progressively raise its yield strength. The complete disappearance of austenite via cold work altogether eliminates the plateau (austenite to martensite transformation) on the stress strain curve, and results in a unique stress strain curve without a classic perfectly linear slope and without an apparent yield point.

While linear binary NiTi is highly durable with good flexibility, binary NiTi may not be an ideal material for certain medical devices due to its inherently low stiffness [i.e., secant modulus around 5 Msi (~34 GPa) at 4% elongation versus an elastic modulus of approximately 28 Msi (~193 GPa) for 316L austenitic stainless steel]. For example, the low modulus of the material in the martensitic condition (either linear pseudo-elastic martensite or stress-induced martensite found in superelastic Ni—Ti) relative to an austenitic stainless steel makes it challenging to torque a guide wire made from linear pseudo-elastic Ni—Ti alloy because it has a greater tendency to elastically absorb a significant amount of applied twist as opposed to directly transmitting torque from end to end. Further, Ni—Ti has only moderate plateau stress levels, and is therefore less resistant to bending forces (as compared to stainless steel), and thus less effective at providing support as a guide wire for catheter delivery or as a stent for arterial scaffolding.

BRIEF SUMMARY

The present disclosure describes medical devices that include a Ni—Ti ternary alloy and methods for their manufacture. The medical devices described herein include at least one part fabricated from the Ni—Ti ternary alloy. In the Ni—Ti alloys, the ternary alloying element is selected to be compatible with Ni—Ti. This is significant because titanium is a notoriously reactive element and readily forms intermetallic compounds when combined with many elements. Nevertheless, by virtue of their compatibility with titanium, additions of the ternary alloying element(s) substitute for titanium in the Ni—Ti phase up to the solubility of the ternary element and the remainder can exist as a second phase whose mechanical properties resemble that of the pure ternary element and whose elastic modulus exceeds that of the Ni—Ti matrix. The resulting ternary alloys typically have an elastic modulus, which can be estimated using the "rule of mixtures," somewhere in between the moduli of the first and second phases.

In one embodiment, a medical device is described. The medical device includes a body, at least a portion of the body being fabricated from a nickel-titanium (Ni—Ti) alloy comprising nickel (Ni), titanium (Ti), and a ternary alloying element selected from the group consisting of tantalum (Ta), hafnium (Hf), vanadium (V), zirconium (Zr), and combinations thereof. In one embodiment, the ternary alloying element may be present in the Ni—Ti alloy in an amount ranging from about 4 atomic % (at %) to about 30 at %.

In the Ni—Ti alloy, addition of the ternary element results in an alloy having a first phase rich in Ni—Ti and a second phase rich in the ternary alloying element. Above the solid solubility limit of the ternary alloying element in the Ni—Ti matrix, it is believed that incremental additions of the ternary alloying element simply generate more of the second phase rather than altering the composition of the Ni—Ti matrix. In one embodiment, the ternary alloys has one or more of: an elastic modulus in an austenite phase of greater than about 85 GPa, an elastic modulus in a martensite phase of greater than about 42 GPa, or a martensite transformation (Ms) temperature of less than about −5° C.

In another embodiment, a medical implant or medical device is disclosed. The medical implant or medical device includes one or more components at least partially fabricated from a nickel-titanium (Ni—Ti) alloy that includes nickel (Ni), titanium (Ti), and a ternary alloying element selected from the group consisting of tantalum (Ta), hafnium (Hf), vanadium (V), zirconium (Zr), and combinations thereof. The Ni—Ti alloy has a bulk phase rich in Ni—Ti and a secondary phase rich in the ternary alloying element. The Ni—Ti alloy has one or more of an elastic modulus in an austenitic phase of greater than about 85 GPa, an elastic modulus in a martensitic phase of greater than about 42 GPa, or a martensite transformation (Ms) temperature of less than about −5° C.

In one embodiment, the bulk phase (i.e., the Ni—Ti rich phase) has an elastic modulus in an austenite phase ranging from about 75-83 GPa and has an elastic modulus in an martensite phase ranging from about 28-40 GPa. In contrast, the secondary phase has an elastic modulus ranging from about 78-186 GPa. The elastic modulus of the Ni—Ti ternary alloys discussed herein have an elastic modulus that is considerably higher binary Ni—Ti alone. The bulk properties of the Ni—Ti ternary alloys described herein may typically accounted for by the so-called "rule of mixtures," which describes the properties of a composite in terms of a volume weighted average of the properties of each of the individual phases (i.e., the bulk phase and the secondary phase).

In yet another embodiment, a method for fabricating a medical implant or medical device is disclosed. The method includes (1) providing a nickel-titanium (Ni—Ti) alloy ingot that comprises nickel (Ni), titanium (Ti), and a ternary alloying element selected from the group consisting of tantalum (Ta), hafnium (Hf), vanadium (V), zirconium (Zr), and combinations thereof. In one embodiment, the ternary alloying element is included in an amount sufficient to yield an ingot that has a two phase structure showing primary dendrites of a first phase rich in Ni—Ti and a eutectic structure comprised of both the first phase and a second phase rich in the ternary alloying element. The method further includes (2) fabricating one or more components of the medical implant or medical device from the Ni—Ti alloy ingot to yield a structure in which the primary dendrites of the first phase and the eutectic structure are oriented in the working direction and elongated correspondingly. The one or more components of the medical implant or medical device fabricated from the Ni—Ti alloy have one or more of an elastic modulus in an austenitic phase of greater than about 85 GPa, an elastic modulus in a martensitic phase of greater than about 42 GPa, or a martensite transformation temperature of less than about −5° C.

These and other objects and features of the present disclosure will become more fully apparent from the following description and appended claims, or may be learned by the practice of the embodiments of the invention as set forth hereinafter.

BRIEF DESCRIPTION OF THE DRAWINGS

To further clarify the above and other advantages and features of the present disclosure, a more particular description of the invention will be rendered by reference to specific embodiments thereof which are illustrated in the appended drawings. It is appreciated that these drawings depict only illustrated embodiments of the invention and are therefore not to be considered limiting of its scope. Embodiments of the invention will be described and explained with additional specificity and detail through the use of the accompanying drawings in which:

FIG. 5 is a side view of a stent embodying features of the invention, wherein the stent is in an unexpanded state;

FIG. 6 is a side view of the stent of FIG. 6 in an expanded condition, depicting cylindrical rings connected by undulating links;

DETAILED DESCRIPTION

I. Introduction

Figure 1:
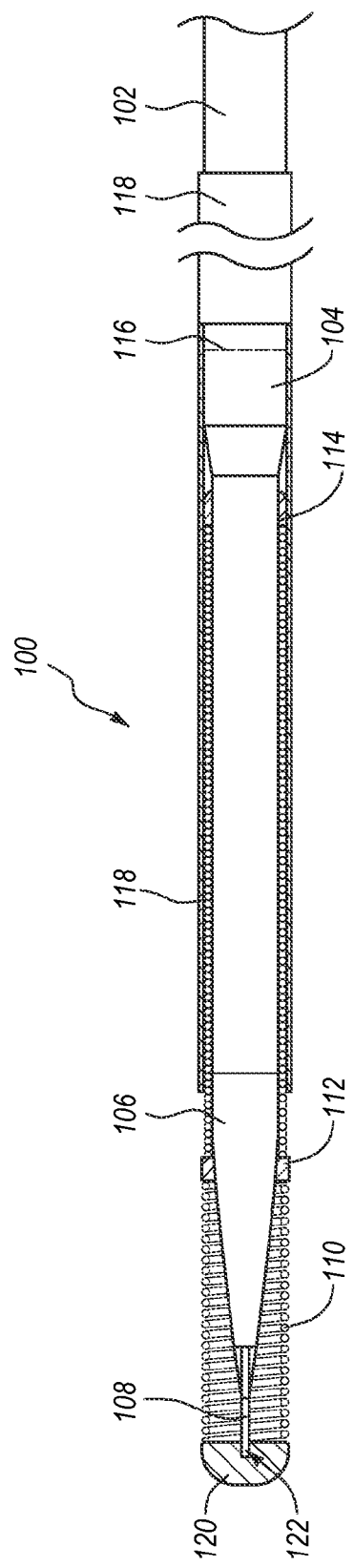
FIG. 1 illustrates a partial cut-away view of a guide wire device according to one embodiment of the present disclosure.

The present disclosure describes medical devices that include a Ni—Ti ternary alloy and methods for their manufacture. The medical devices described herein include at least one part fabricated from the Ni—Ti ternary alloy. In the Ni—Ti alloys, the ternary alloying element is selected to be compatible with Ni—Ti. This is significant because titanium is a notoriously reactive element and readily forms intermetallic compounds when combined with many elements. Nevertheless, by virtue of their compatibility with titanium, additions of the ternary alloying element(s) substitute for titanium in the Ni—Ti phase up to the solubility of the ternary element and the remainder can exist as a second phase whose mechanical properties resemble that of the pure ternary element and whose elastic modulus exceeds that of the Ni—Ti matrix.

Because of the presence of the ternary alloying element, the Ni—Ti alloy disclosed herein has an elastic modulus (also referred to as Young's modulus) that is considerably higher than comparable binary Ni—Ti alloy under otherwise similar conditions (e.g., same level of cold work, etc.). For example, the resulting ternary alloys may have an elastic modulus, which can be estimated using the "rule of mixtures," somewhere in between the moduli of the first and second phases. Elastic modulus is increased as compared to the comparable binary Ni—Ti alloy for both austenitic and martensitic states.

II. Ni—Ti Ternary Alloys

Embodiments of the present invention provide medical devices that include one or more components fabricated from Ni—Ti ternary alloys that possess substantially greater elastic modulus and shear modulus than binary nitinol. Greater elastic and shear moduli may be found in the superelastic, linear pseudo elastic, and shape memory phases. For instance, alloys having linear pseudoelastic characteristics and a high elastic modulus and shear modulus facilitate torque transmission, steerability, and shapability of guide wire devices to facilitate the advancing of the guide wire in a body lumen. The linear pseudoelastic Ni—Ti alloys exhibit extensive, recoverable strain, which greatly minimizes the risk of performance loss due to kinking with possible concomitant damage to arteries during the advancement therein. In another example, stents and other intraluminal devices formed from high modulus superelastic, shape memory Ni—Ti ternary alloys may be better able to scaffold vessels and resist compressive forces as compared to comparable devices made from binary Ni—Ti.

An example of a Ni—Ti ternary alloys is the family of alloys containing nickel (Ni), titanium (Ti), and a ternary alloying element selected from the group consisting of tantalum (Ta), hafnium (Hf), vanadium (V), zirconium (Zr), scandium (Sc), yttrium (Y) and combinations thereof. In one embodiment, the ternary alloying element in present in the Ni—Ti alloy in an amount ranging from greater than or equal to the solid solubility limit (e.g., about 2-6 atomic % (at %)) of the ternary alloying element in the Ni—Ti matrix up to about 30 at %.

At some component ratios, the Ni—Ti ternary alloy may form a dual phase microstructure. The preferred dual phase microstructure consists of a Ni—Ti rich primary phase and a dispersed second phase, consisting largely of the ternary alloying element, which naturally arises by virtue of a quasi-binary eutectic reaction during solidification. For example, the ternary alloying element may displace some percentage of the Ti in the Ni—Ti matrix (e.g., about 3 at %), which gives rise to a Ni—Ti matrix that contains, for example, about 3 at % of the ternary element, with excess ternary element settling out as the second phase. In another example, the ternary alloying element may displace some percentage of the Ni in the Ni—Ti matrix (e.g., about 3 at %), which gives rise to a Ni—Ti matrix that contains, for example, about 3 at % of the ternary element, with excess ternary element settling out as the second phase. In yet another example, the ternary alloying element may displace some percentage of both Ni and Ti in the Ni—Ti matrix (e.g., about 1-2 at % of each), which gives rise to a Ni—Ti matrix that contains, for example, about 3 at % of the ternary element, with excess ternary element settling out as the second phase. And while the primary phase and the dispersed phase may include the same components, the ternary element content will generally be much higher in the dispersed phase as compared to the primary phase. In a preferred embodiment, the second phase rich in the ternary alloying element is ductile and coherent with the primary Ni—Ti phase.

In some cases, the dual phase microstructure exhibits qualities of a so-called metal matrix composite. The term metal matrix composite (MMC) encompasses a wide range of scales and microstructures; however, the bulk properties of an MMC are typically accounted for by the so-called "rule of mixtures," which describes the properties of a composite in terms of a volume weighted average of the properties of each of the individual phases (i.e., the primary and dispersed phases). While the rule of mixtures is to some extent an approximation, it does provide a useful metric for understanding the properties of the Ni—Ti ternary alloys described herein. For example, the observed elastic modulus of the bulk alloy may be described as a volume weighted average of the elastic moduli of the Ni—Ti rich phase and the second phase rich in the ternary alloying element.

Figure 13A:
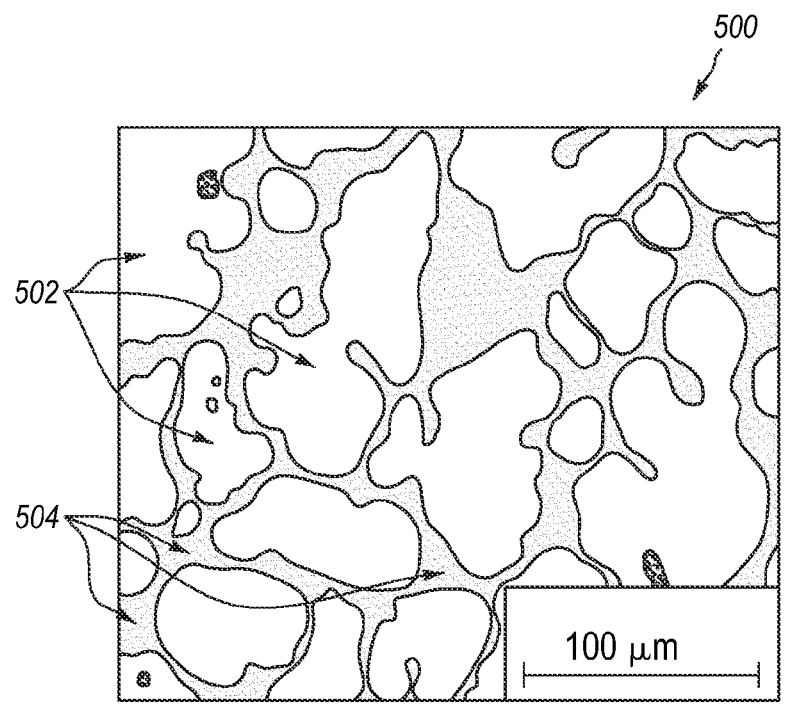
FIG. 13A shows schematically an exemplary as cast Ni—Ti ternary alloy micro-structure in which primary dendrites of a first NiTi rich phase plus a eutectic mixture of the first phase and a second Nb rich phase are present.
Figure 13B:
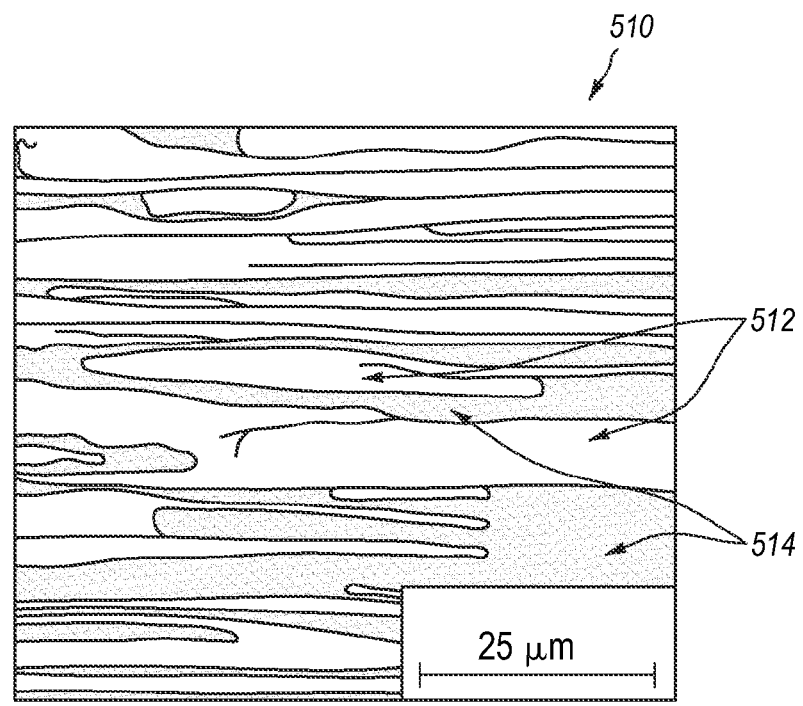
FIG. 13B shows schematically how the Ni—Ti ternary alloy forms an elongated microstructure comprised of the Ni—Ti rich primary phase and the eutectic mixture of both phases upon rolling (e.g., hot rolling) of the dual phase microstructure of FIG. 13A

The dual phase Ni—Ti ternary alloy system includes two ductile phases having widely different mechanical properties. Cast ingots of the Ni—Ti ternary alloy may contain primary dendrites of the Ni—Ti rich first phase 502 surrounded by a eutectic mixture of both phases 504 (FIG. 13A). Upon working down the cast material 500 to produce a guide wire or other intra-corporal body structure (e.g., by one or more of drawing, stamping, rolling, flattening, swaging, or other suitable working techniques), the dendrites 502 and eutectic mixture 504 begin to be elongated in the working direction, resulting in a microstructure which is not completely homogenous, and that is comprised of small second phase particles that are rich in the ternary alloying element surrounded by the Ni—Ti rich first phase. In one embodiment (FIG. 13B), the structure 510 is comprised of thin elongate bands 512 of the first Ni—Ti rich phase surrounded by thin bands of the eutectic mixture 514. Such a structure may be directional (e.g., in the direction of the rolling, drawing, etc.).

Where the superelastic or linear pseudo-elastic structure is induced within the Ni—Ti-rich phase, the observed properties of the bulk material are a blend of what would be predicted from a mixture of the individual properties of the Ni—Ti phase and nearly pure ternary alloying element (e.g., nearly pure tantalum). By way of example, Ni—Ti—Nb alloy systems have been well studied and some general principles of the alloys discussed herein can be ascertained by reviewing Ni—Ti—Nb alloy systems. For further discussion of Ni—Ti—Nb alloy systems see, e.g., Eutectic Liquid Formation in the NiTi—Nb System: New Joining Method for Nitinol Point, Ke-Bin Low et al., Proceedings of the International Conference on Shape Memory and Superelastic Technologies (2008) pp. 829-836. Nonetheless, it is worth mentioning that the compositions discussed herein (i.e., Ni—Ti ternary alloys is the family of alloys containing nickel (Ni), titanium (Ti), and a ternary alloying element selected from the group consisting of tantalum (Ta), hafnium (Hf), vanadium (V), zirconium (Zr), scandium (Sc), yttrium (Y), and combinations thereof) do not appear in the Ke-Bin Low reference incorporated above.

If one were attempting to formulate new Ni—Ti ternary alloys, one approximation would be to constrain the Ni and Ti compositions such that the amount of Ni exceeds the amount of Ti by an amount somewhere in the range of the solid solubility limit of the ternary alloying element in the Ni—Ti matrix (e.g., about 2 at % to 6 at %). Suitable examples of Ni—Ti ternary alloys may include about 36 at % to about 51 at % Ni, about 32 at % to about 47 at % Ti, and about 4 at % to about 30 at % of the ternary alloying element. In another embodiment, the ternary alloy described herein may include 36, 37, 38, 39, 40, 41, 42, 43, 44, 45, 46, 47, 48, 49, 50, or 51 at % Ni, 32, 33, 34, 35, 36, 37, 38, 39, 40, 41, 42, 43, 44, 45, 46, or 47 at % Ti, 4, 5, 6, 7, 8, 9, 10, 11, 12, 13, 14, 15, 16, 17, 18, 19, 20, 21, 22, 23, 24, 25, 26, 27, 28, 29, or 30 at % of the ternary alloying element, and any combination of the above listed amounts of Ni, Ti, and the ternary alloying element.

Another approximation would be to constrain the Ni and Ti compositions such that the amount of Ti exceeds the amount of Ni by an amount somewhere in the range of the solid solubility limit of the ternary alloying element in the Ni—Ti matrix (e.g., about 2 at % to 6 at %). Suitable examples of Ni—Ti ternary alloys may include about 36 at % to about 51 at % Ti, about 32 at % to about 47 at % Ni, and about 4 at % to about 30 at % of the ternary alloying element. In another embodiment, the ternary alloy described herein may include 36, 37, 38, 39, 40, 41, 42, 43, 44, 45, 46, 47, 48, 49, 50, or 51 at % Ti, 32, 33, 34, 35, 36, 37, 38, 39, 40, 41, 42, 43, 44, 45, 46, or 47 at % Ni, 4, 5, 6, 7, 8, 9, 10, 11, 12, 13, 14, 15, 16, 17, 18, 19, 20, 21, 22, 23, 24, 25, 26, 27, 28, 29, or 30 at % of the ternary alloying element, and any combination of the above listed amounts of Ni, Ti, and the ternary alloying element.

Yet another approximation would be to constrain the Ni and Ti compositions based on the assumption that the ternary alloying element substitutes for both Ti and Ni in the Ni—Ti matrix and to reduce both by an amount somewhere in the range of the solid solubility limit of the ternary alloying element in the Ni—Ti matrix (e.g., about 2 at % to 6 at %). Suitable examples of Ni—Ti ternary alloys may include about 35 at % to about 48 at % Ti, about 35 at % to about 48 at % Ni, and about 4 at % to about 30 at % of the ternary alloying element. In another embodiment, the ternary alloy described herein may include 35, 36, 37, 38, 39, 40, 41, 42, 43, 44, 45, 46, 47, or 48 at % Ti, 35, 36, 37, 38, 39, 40, 41, 42, 43, 44, 45, 46, 47, or 48 at % Ni, 4, 5, 6, 7, 8, 9, 10, 11, 12, 13, 14, 15, 16, 17, 18, 19, 20, 21, 22, 23, 24, 25, 26, 27, 28, 29, or 30 at % of the ternary alloying element, and any combination of the above listed amounts of Ni, Ti, and the ternary alloying element.

In the above listed compositions, some adjustment in the ratio of Ni to Ti may be preferred to fine tune the transformation temperature of the Ni—Ti-rich phase and thus its ability to be processed to provide the desired superelastic, shape memory, or linear elastic martensite behavior.

In an embodiment, the martensite transformation ($M_s$) temperature of the Ni—Ti ternary alloy is less than about −5° C., less than about −10° C., less than −15° C., less than −25° C., or less than −40° C. Higher Ni to Ti ratios generally correspond to decreased $M_s$ temperature in binary alloys, and similar behavior is expected with the described ternary alloy systems but with the added complexity that ternary additions can substitute for primarily for Ni, primarily for Ti, or for both Ni and Ti.

In one embodiment, the Ni—Ti rich phase may have a an elastic modulus in an austenite phase ranging from about 75-83 GPa and an elastic modulus in an martensite phase ranging from about 28-40 GPa. The second phase rich in the ternary alloying element has an elastic modulus ranging from about 78-186 GPa. Therefore, Ni—Ti ternary alloy has an elastic modulus in an austenitic phase of greater than about 85 GPa and an elastic modulus in a martensitic phase of greater than about 42 GPa.

For example, the Ni—Ti ternary alloy may have an elastic modulus of about 50 gigapascals (GPa) to about 100 GPa or about 60 gigapascals (GPa) to about 70 GPa in the martensitic phase. In another example, the Ni—Ti ternary alloy may have an elastic modulus of about 85 gigapascals (GPa) to about 150 GPa or about 95 gigapascals (GPa) to about 135 GPa in the austenitic phase.

II. Medical Devices

In ordinary applications, differences in elastic modulus between two materials can be readily compensated for by dimensional alterations. That is, for example, the inherent floppiness of a wire material that has a low elastic modulus can ordinarily be compensated for by increasing the diameter of the wire in order to attain equivalent deflection behavior when compared to a wire material with a higher elastic modulus. However, intra-corporal medical devices typically face inherent dimensional constraints that are imposed by the overall product profile, the size of the anatomy to be accessed and similar factors. For this reason, the Ni—Ti ternary alloys discussed herein, which have higher stiffness characteristics than comparable binary Ni—Ti, significantly expand the maximum range of torsional or bending stiffness that can be achieved in a guide wire or other intra-corporal medical device of a given profile.

Medical devices, according to one or more embodiments of the invention described herein, include, but are not limited to, guide wires, stents, embolic protection filters, and graft assemblies. Such devices (or portions thereof) can be formed from the described Ni—Ti ternary alloy(s) so as to benefit from increased elastic modulus, shear modulus, and plateau stress levels.

For example, guide wire devices are used in minimal invasive procedures such as, but not limited to, percutaneous transluminal coronary angioplasty (PTCA) to track through vessels, access and cross lesions, and support interventional devices for a variety of procedures. Guide wire devices have a number of desired performance characteristics such as, but not limited to, flexibility, support, the ability to steer the guide wire device through the patient's vasculature (i.e., trackability), the ability to transmit steering torque from the proximal end of the device outside the patient's body to the distal tip inside (i.e., torqueability), torque control, lubricity, the ability to visualize the guide wire device as it progresses through the patient's body, and tactile feedback. Guide wire design typically involves the balancing of these various characteristics.

In order to, for example, track through a patient's vasculature, guide wire devices are quite long and thin. In terms of length, guide wire devices need to be long enough to travel from an access point outside a patient's body to a treatment site and narrow enough to pass freely through the patient's vasculature. Lengths of about 150 cm to about 300 cm are typical. In terms of diameter, typical guide wire devices have an overall diameter of about 0.2 mm to about 0.5 mm for coronary use. Larger diameter guide wires may be employed in peripheral arteries and other relatively larger body lumens. The diameter of the guide wire device affects its flexibility, support, and torque. Thinner wires are more flexible and are able to access narrower vessels while larger diameter wires offer greater support and torque transmission. While stiffness, elastic modulus, and shear modulus may be increased by increasing wire diameter, such larger diameter wires are not physically sized to be readily insertable into the small size vasculature of the typical patient. As such, material properties, rather than physical size, can be manipulated in order to achieve more desirable stiffness characteristics.

Requirements for stents, embolic protection filters, graft assemblies and similar implantable medical devices similarly benefit from increased elastic modulus and shear modulus, as well as a higher plateau stress level where the alloy has super-elastic characteristics.

A. Guide Wire Devices

In an embodiment, one or more portions of a guide wire device that may be fabricated from a Ni—Ti ternary alloy is described. The guide wire device includes an elongated shaft member having a proximal section and a distal section. At least a portion of the elongated shaft member is fabricated from a nickel-titanium (Ni—Ti) alloy that includes nickel (Ni), titanium (Ti), and a ternary alloying element selected from the group consisting of tantalum (Ta), hafnium (Hf), vanadium (V), zirconium (Zr), and combinations thereof. In an embodiment, the ternary alloying element may be included in the Ni—Ti ternary alloy in an amount greater than or equal to the solid solubility limit of the ternary alloying element in the Ni—Ti matrix (e.g., about 4 atomic % ("at %")) up to about 30 at %.

The Ni—Ti ternary alloy disclosed herein has considerably higher elastic moduli values (i.e., Young's modulus and shear modulus) as compared to equiatomic or near-equiatomic Ni—Ti in both austenitic and martensitic phases. The Ni—Ti ternary alloy disclosed herein may exhibit super-elastic characteristics. In another embodiment, the alloy may be cold worked to a sufficiently high degree without subsequent heat treatment or with minimal heat treatment so that the alloy exhibits linear pseudoelastic behavior rather than super-elastic behavior. In one embodiment, the Ni is present in the Ni—Ti alloy in an amount higher than a corresponding amount of Ti, with the balance of the Ni—Ti phase being made up of the ternary alloying element. Such manipulation of the Ni—Ti ratio may further decrease the martensitic transformation temperature ($M_s$), effectively increasing the plateau stress level due to the increased difference between the $M_s$ temperature and the intended service temperature (e.g., body temperature).

Referring now to FIG. 1, a partial cut-away view of an example of a guide wire device 100 that embodies features of the invention is illustrated. The guide wire device 100 may be adapted to be inserted into a patient's body lumen, such as an artery or another blood vessel. The guide wire device 100 includes an elongated proximal portion 102 and a distal portion 104. In one embodiment, both the elongated proximal portion 102 and the distal portion 104 may be formed from a Ni—Ti ternary alloy. In another embodiment, the elongated proximal portion 102 may be formed from a first material such as stainless steel (e.g., 316L stainless steel) or a Ni—Ti alloy and the distal portion may be formed from a second material such as a Ni—Ti ternary alloy. In embodiments where the elongated proximal portion 102 and the distal portion 104 are formed from different materials, the elongated proximal portion 102 and the distal portion 104 may coupled to one another via a welded or other joint 116 that couples the proximal portion 102 and the distal portion 104 into a torque transmitting relationship.

In an embodiment, selected portions of the guide wire device 100 or the entire guide wire device 100 may be fabricated from a superelastic Ni—Ti ternary alloy. Because the Ni—Ti ternary alloys described herein have higher elastic moduli and, in some embodiments, a higher plateau stress, such alloys will feel considerably stiffer and be easier to steer than comparable binary Ni—Ti. Such alloys are highly durable by virtue of the fact that they can be exposed to upwards of 8% elastic strain without permanently deforming. Likewise, such alloys are highly corrosion resistant and biocompatible.

In another embodiment, selected portions of the guide wire device 100 or the entire guide wire device 100 may be cold worked in order to yield a linear pseudo-elastic microstructure. As mentioned, increasing levels of cold-work (i.e., permanent deformation without subsequent heat treatment) progressively raises the yield strength of the material and leads to almost the complete disappearance of austenite and the elimination of the plateau (austenite to martensite transformation) on the stress strain curve, resulting in a unique stress strain curve without a classic linear modulus of elasticity and without an apparent yield point.

For example, in an embodiment, selected portions of the guide wire device 100 or the entire guide wire device 100 may be cold worked to impart a linear pseudo-elastic microstructure that includes at least about 40% cold work, or at least about 50% cold work. In another example, about 20% to about 90% cold work, about 30% to about 65% cold work, about 40% cold work to about 50% cold work, or about 45% cold work may be provided. Depending on the composition of the Ni—Ti ternary alloy and the amount of cold work, the Ni—Ti ternary alloy may have an elastic modulus of about 50 gigapascals (GPa) to about 100 GPa or an elastic modulus of about 60 GPa to about 70 GPa. In an embodiment, the Ni—Ti—Nb alloy exhibits a Young's modulus in an austenite phase that is greater than about 85 GPa (greater than binary Ni—Ti), and a Young's modulus in a martensite phase that is greater than about 42 GPa (greater than binary Ni—Ti).

Referring again to FIG. 1, the distal portion 104 may have at least one tapered section 106 that, in the illustrated embodiment, becomes smaller in the distal direction. The length and diameter of the tapered distal core section 106 can, for example, affect the trackability of the guide wire device 100. Typically, gradual or long tapers produce a guide wire device with less support but greater trackability, while abrupt or short tapers produce a guide wire device that provides greater support but also greater risk of prolapse (i.e., kink) when steering.

In the illustrated embodiment, the tapered distal core section 106 may further include a user shapeable distal end section 108. Ni—Ti alloys such as the Ni—Ti ternary alloys discussed may be shapeable (i.e., capable of being permanently deformed) in the linear pseudo-elastic state. The linear pseudo-elastic state can be imparted to the Ni—Ti alloy by cold work, with varying amounts of cold work imparting different degrees of linear pseudo-elasticity and differing degrees of shapeability. In contrast to superelastic Ni—Ti alloy, linear pseudo-elastic Ni—Ti alloy can readily be permanently deformed by stressing the material beyond its elastic strain limit. As such, the shapeable distal end section 108 can allow a practitioner to shape the distal and of the guide wire device 100 to a desired shape (e.g., a J-bend) for tracking through the patient's vasculature.

In an embodiment, the distal end section 108 is manufactured by grinding the distal end of the Ni—Ti distal section 104 to a first cross-sectional dimension (e.g., by centerless grinding). The distal end section 108 may be made shapeable by cold-working (e.g., by flattening) the ground portion to a second cross-sectional dimension. For example, the first dimension can be in a range from about 0.1 mm to about 0.07 mm, or about 0.08 mm. The second cross-sectional dimension, which is formed by, for example, cold-work flattening at least a part of the ground distal section, may be in a range from about 0.065 mm to about 0.008 mm, about 0.055 mm to about 0.03 mm, about 0.05 to about 0.04 mm, or about 0.045 mm.

The length of the distal end section 106 can, for example, affect the steerability of the guide-wire device 100. In one embodiment, the distal end section 106 is about 10 cm to about 40 cm in length. In another embodiment, the distal end section 106 is about 2 to about 6 cm in length, or about 2 to 4 cm in length.

As illustrated in FIG. 1, the guide wire device 100 includes a helical coil section 110. The helical coil section 110 affects support, trackability, and visibility of the guide wire device and provides tactile feedback. In some embodiments, the most distal section of the helical coil section 110 is made of radiopaque metal, such as platinum or a platinum-nickel or platinum-iridium alloy, to facilitate the observation thereof while it is disposed within a patient's body. As illustrated, the helical coil section 110 may be disposed about at least a portion of the distal portion 104 and may have a rounded, atraumatic cap section 120 on the distal end thereof. The helical coil section 110 may be secured to the distal portion 104 at proximal location 114 and at intermediate location 112 by a suitable technique such as, but not limited to, soldering, brazing, or welding.

In one embodiment, the distal end section 108 may be secured to the rounded, atraumatic cap section 120 by virtue of a joint 122 such as, but not limited to, a soldered, brazed, or welded joint. Because Ni—Ti alloy forms a persistent oxide layer, it can be difficult to solder Ni—Ti. Therefore, in one embodiment, the distal end section 108 may be joined to the atraumatic cap section 120 using a soldering technique specially adapted to soldering Ni—Ti alloys. Briefly stated here, the distal end section 108 may be prepared and a layer of solder material may be applied thereto and the distal end section 108 may be soldered to the rounded, atraumatic cap section 120 to form a soldered joint 122.

In one embodiment, portions of the guide wire device 100 are coated with a coating 118 of lubricous material such as polytetrafluoroethylene (PTFE) (sold under the trademark Teflon by du Pont, de Nemours & Co.) or other suitable lubricous coatings such as the polysiloxane coatings, polyvinylpyrrolidone (PVP), and the like.

Figure 2A:
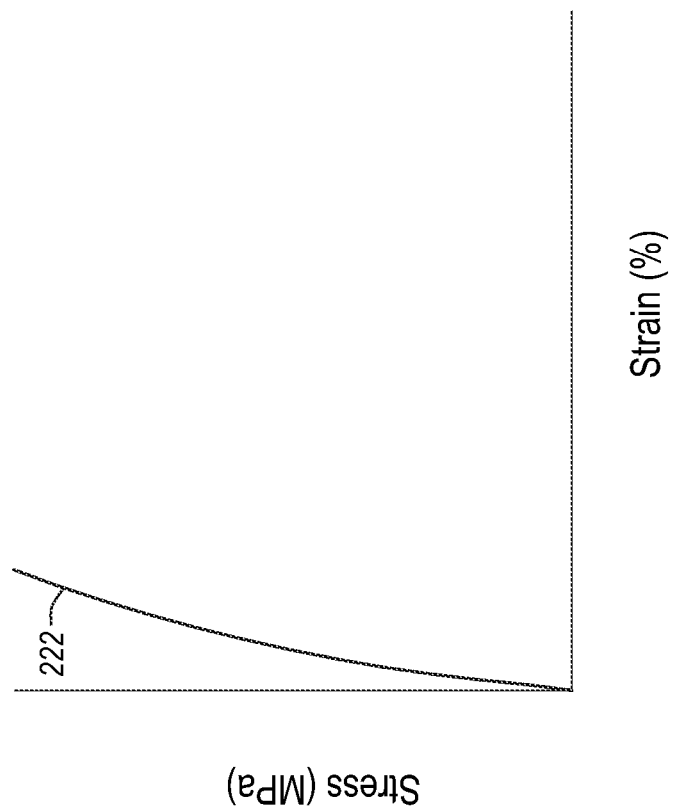
FIGS. 2A-2C shows stress-strain curves for various materials.
Figure 2B:
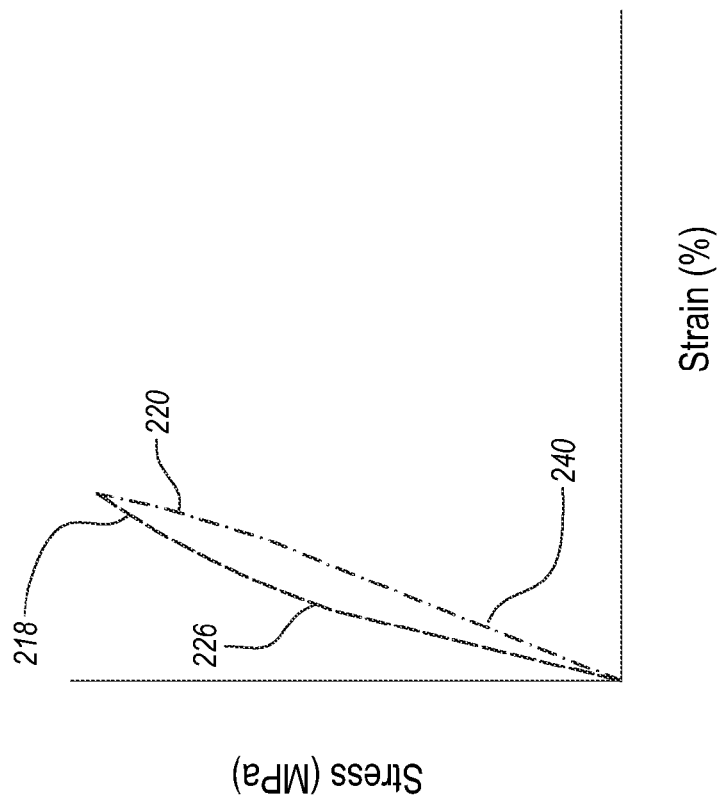
Figure 2C:
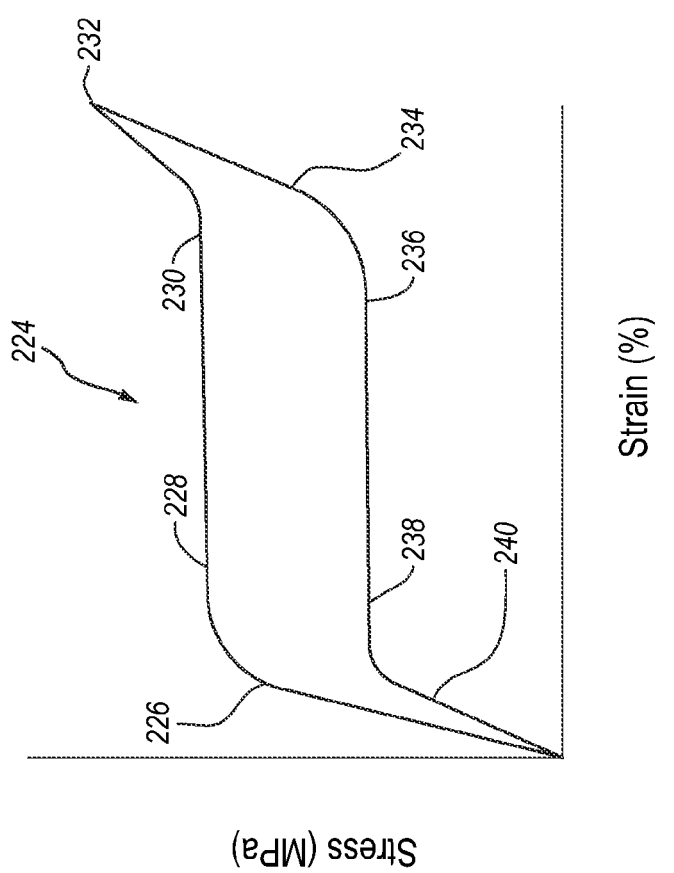

To illustrate the foregoing points, FIGS. 2A-2C show the elastic component of three idealized stress-strain curves for 316L stainless steel (FIG. 2A—curve 222), a linear pseudo-elastic Ni—Ti—Nb alloy (FIG. 2B—curves 218 and 220), and a super-elastic Ni—Ti alloy (FIG. 2C—curve 224). The stress/strain relationship is plotted on x-y axes, with the x axis representing strain and the y axis representing stress.

In curve 224, when stress is applied to a specimen of a metal such as Ni—Ti or a Ni—Ti alloy exhibiting super-elastic characteristics at a temperature at or above the temperature at which the transformation of the martensitic phase to the austenitic phase is complete, the specimen deforms elastically (curve portion 226) until it reaches a particular stress level where the alloy then undergoes a stress-induced phase transformation from the austenitic phase to the martensitic phase (i.e., the stress-induced martensite phase). As the phase transformation progresses, the alloy undergoes significant increases in strain with little or no corresponding increases in stress. On curve 224, this is represented by the upper, nearly flat stress plateau 228 (e.g., at approximately 70 to 80 ksi). The strain increases while the stress remains essentially constant until the transformation of the austenitic phase to the martensitic phase is complete (at curve portion 230). Thereafter, further increase in stress is necessary to cause further deformation (curve portion 232). The martensitic metal first yields elastically upon the application of additional stress and then plastically with permanent residual deformation (not shown).

If the load on the specimen is removed before any permanent deformation has occurred, the martensite specimen elastically recovers and transforms back to the austenitic phase. The reduction in stress first causes a decrease in stress (curve portion 234). As stress reduction reaches the level at which the martensitic phase transforms back into the austenitic phase (curve portion 236), the stress level in the specimen remains essentially constant (curve portion 238), but at a lower level than the constant stress level at which the reverse transformation occurred. In other words, there is significant recovery in strain with only negligible corresponding stress reduction. This is represented in curve 224 by the lower stress plateau 238 (e.g., at about 20 ksi).

After the transformation back to austenite is complete, further stress reduction results in elastic strain reduction (curve portion 240). This ability to incur significant strain at relatively constant stress upon the application of a load and to recover from the deformation upon the removal of the load is commonly referred to as super-elasticity or non-linear pseudo-elasticity. The area between or bounded by the upper plateau 228 and lower plateau 238 represents the hysteresis in the super-elastic Ni—Ti alloy.

FIG. 2B shows a curve 218-220 representing the idealized behavior of Ni—Ti—Nb alloy which has been cold worked so as to inhibit any further stress induced phase transformation (i.e., it exhibits so called linear pseudo-elastic behavior). While curves 218 and 220 may be typically be described as "linear" by those in the art, it is readily apparent that the name is somewhat of a misnomer, as there may be noticeable curvature to the curve. Curve 218-220 does not contain any flat plateau stresses, as found in super-elastic curve 224. This stands to reason since the Ni—Ti—Nb alloy of curve 218-220 remains in the martensitic phase throughout stress loading and unloading, and does not undergo any phase change. Curve 218-220 shows that increasing stress begets a proportional increase in reversible strain, and a release of stress begets a proportional decrease in strain. The area bounded between curves 218 and 220 represent the hysteresis in the linear pseudo-elastic Ni—Ti alloy.

With the use of a linear pseudo-elastic Ni—Ti ternary alloy, the mechanical strength of the disclosed medical devices may be substantially greater per unit strain than a comparable device made of super-elastic Ni—Ti alloy. Consequently, a major benefit may be that smaller component parts (e.g., such as the distal end section 108) can be used. A small profile can be a very important factor for crossing narrow lesions or for accessing remote and tortuous arteries.

Even where the Ni—Ti ternary alloy retains super-elastic properties, because of the inclusion of the ternary alloying element and the corresponding increase in elastic modulus, the elastic moduli values for the Ni—Ti ternary alloy are significantly increased as compared to comparable super-elastic binary Ni—Ti. The increased stiffness provides the desired increased torsional transmitting ability, increased stent scaffolding strength, etc., all without requiring increased physical dimensions.

FIG. 2A shows curve 222 that represents the conventional elastic behavior of a standard 316L stainless steel. Stress is incrementally applied to the steel and, just prior to the metal deforming plastically, incrementally released.

Figure 3:
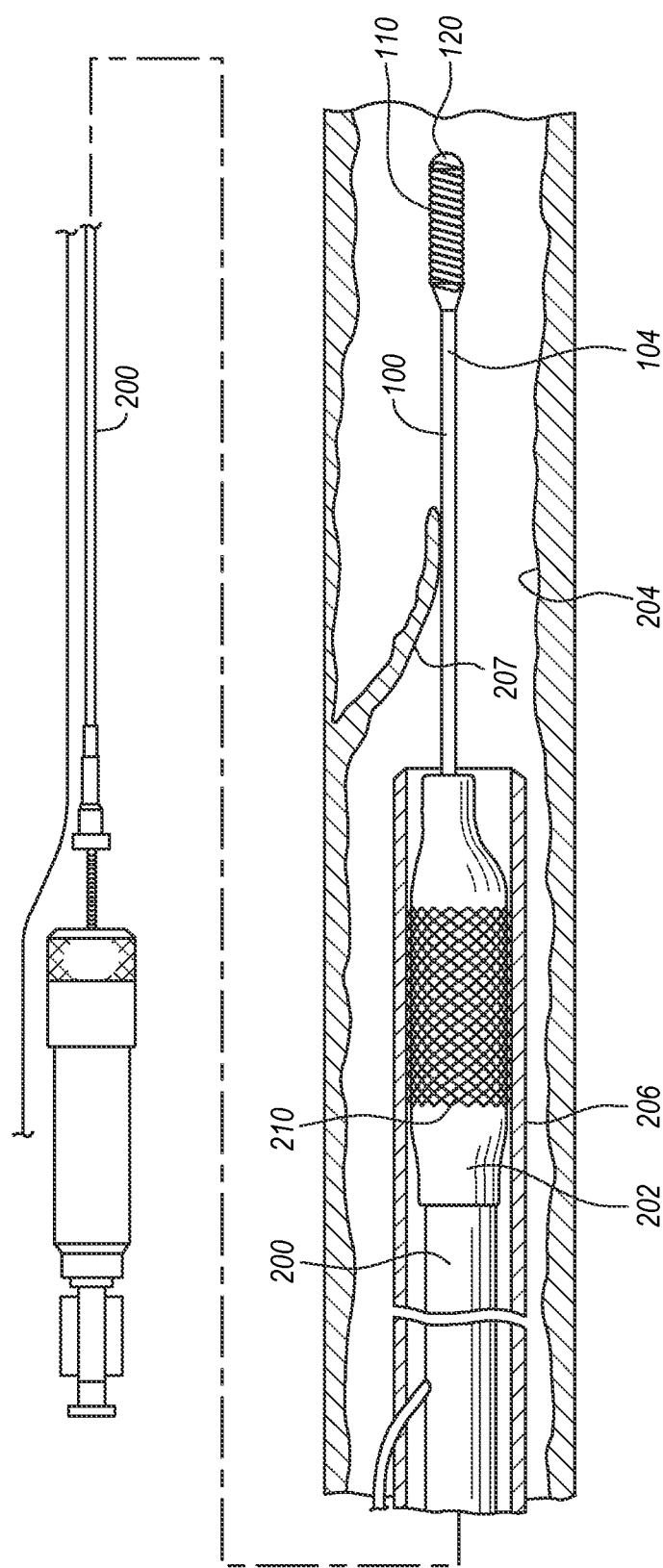
FIG. 3 is a side elevation view, in partial cross-section, of a delivery catheter within a body lumen having a stent disposed about the delivery catheter according to an embodiment of the present disclosure.

Referring now to FIG. 3, the guide wire device 100 is shown configured to facilitate deploying a stent 210. FIG. 3 provides more detail about the manner in which the guide wire device 100 may be used to track through a patient's vasculature where it can be used to facilitate deployment of a treatment device such as, but not limited to, stent 210. FIG. 3 illustrates a side elevation view, in partial cross-section, of a delivery catheter 200 having a stent 210 disposed thereabout according to an embodiment of the present disclosure. The portion of the illustrated guide wire device 100 that can be seen in FIG. 3 includes the distal portion 104, the helical coil section 110, and the atraumatic cap section 120. The delivery catheter 200 may have an expandable member or balloon 202 for expanding the stent 210, on which the stent 210 is mounted, within a body lumen 204 such as an artery. In another embodiment, stent 210 may be self-expanding. For example, a sheath may be initially disposed over stent 210 so as to maintain an un-expanded configuration. When stent 210 is advanced to a desired position, the sheath may be removed and stent 210 expanded.

The delivery catheter 200 may be a conventional balloon dilatation catheter commonly used for angioplasty procedures. The balloon 202 may be formed of, for example, polyethylene, polyethylene terephthalate, polyvinylchloride, nylon, Pebax™ or another suitable polymeric material. To facilitate the stent 210 remaining in place on the balloon 202 during delivery to the site of the damage within the body lumen 204, the stent 210 may be compressed onto the balloon 202. Other techniques for securing the stent 210 onto the balloon 202 may also be used, such as providing collars or ridges on edges of a working portion (i.e., a cylindrical portion) of the balloon 202.

In use, the stent 210 may be mounted onto the inflatable balloon 202 on the distal extremity of the delivery catheter 200. The balloon 202 may be slightly inflated to secure the stent 210 onto an exterior of the balloon 202. The catheter/stent assembly may be introduced within a living subject using a conventional Seldinger technique through a guiding catheter 206. The guide wire 100 may be disposed across the damaged arterial section with the detached or dissected lining 207 and then the catheter/stent assembly may be advanced over the guide wire 100 within the body lumen 204 until the stent 210 is directly under the detached lining 207. The balloon 202 of the catheter 200 may be expanded, expanding the stent 210 against the interior surface defining the body lumen 204 by, for example, permanent plastic deformation of the stent 210. In an embodiment employing a self-expanding stent, removal of a sheath may be sufficient to allow a self-expanding stent to expand against the interior surface defining body lumen 204. In either case, when deployed, the stent 210 holds open the body lumen 204 after the catheter 200 and the balloon 202 are withdrawn.

B. Stent Devices

Figure 4:
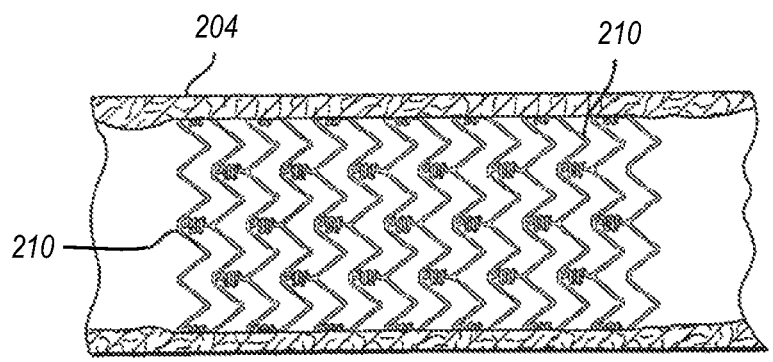
FIG. 4 is an elevational view, partially in section, of a stent embodying features of the invention, wherein the stent is expanded within an artery, so that the stent apposes an arterial wall.

As depicted in FIG. 4, the implanted stent 210 remains in the vessel 204 after the balloon 202 has been deflated and the catheter 200 and guide wire 100 have been withdrawn from the patient.

The stent 210 (which may be formed of the disclosed Ni—Ti ternary alloys) serves to hold open the body lumen 204 after the catheter 200 is withdrawn. Such a stent 210 may be fabricated from an elongated tubular member, where the undulating components of the stent are relatively flat in transverse cross section, so that when the stent 210 is expanded, it is pressed into the wall of the body lumen and as a result does not interfere with the blood flow through the body lumen 204. The stent 210 may be pressed into the wall of the body lumen and may eventually be covered with endothelial cell growth, which further minimizes blood flow interference. The undulating ring portion of the stent 210 provides good tacking characteristics to prevent stent movement within the body lumen. Stent 210 may include closely spaced cylindrical elements at regular intervals for providing uniform support for the wall of the body lumen. Such a configuration may better serve to tack up and hold in place small flaps or dissections in the wall of the body lumen, as illustrated in FIG. 4.

As shown in FIGS. 5-9, the stent 210 may be made up of a plurality of cylindrical rings 212, which extend circumferentially around the stent. The stent has a delivery diameter 214 (FIG. 5), and an implanted diameter 216 (FIG. 6). Each cylindrical ring 212 has a proximal end 242 and a distal end 244. Where the stent is laser cut from a solid tube, there may be no discreet parts, such as the described cylindrical rings. However, it may be beneficial for identification and reference to various parts to refer to the cylindrical rings and the following parts of the stent.

Each cylindrical ring 212 defines a cylindrical plane 246, which is bound by the cylindrical ring proximal end 242, the cylindrical ring distal end 244 and the circumferential extent as the cylindrical ring 212 traverses around the cylinder. Each cylindrical ring includes a cylindrical outer wall surface 248, which defines the outer most surface of the stent 210, and a cylindrical inner wall surface 250, which may define the innermost surface of the stent. The cylindrical plane may follow the cylindrical outer wall surface.

Figure 7:
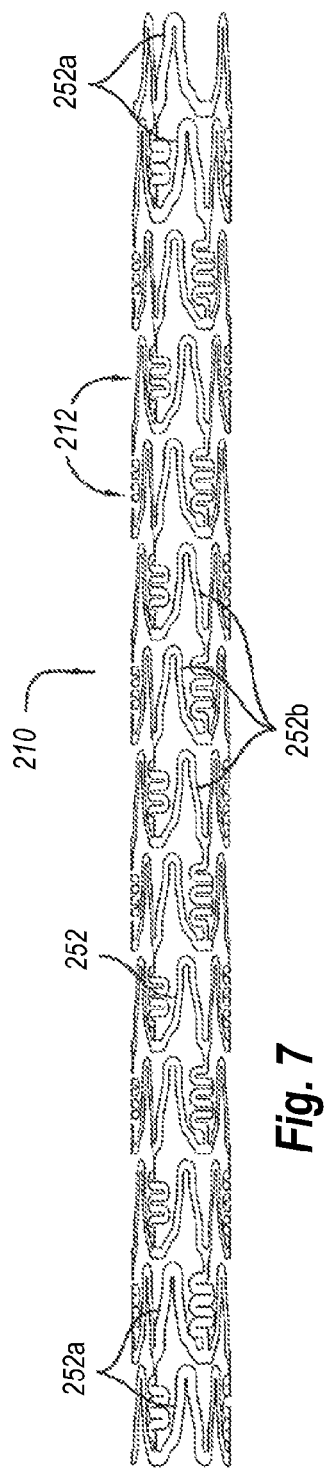
FIG. 7 is a side view of a stent embodying features of the invention, depicting cylindrical rings at the end of the stent having a thicker cross-section than the rings at the center of the stent.
Figure 8:
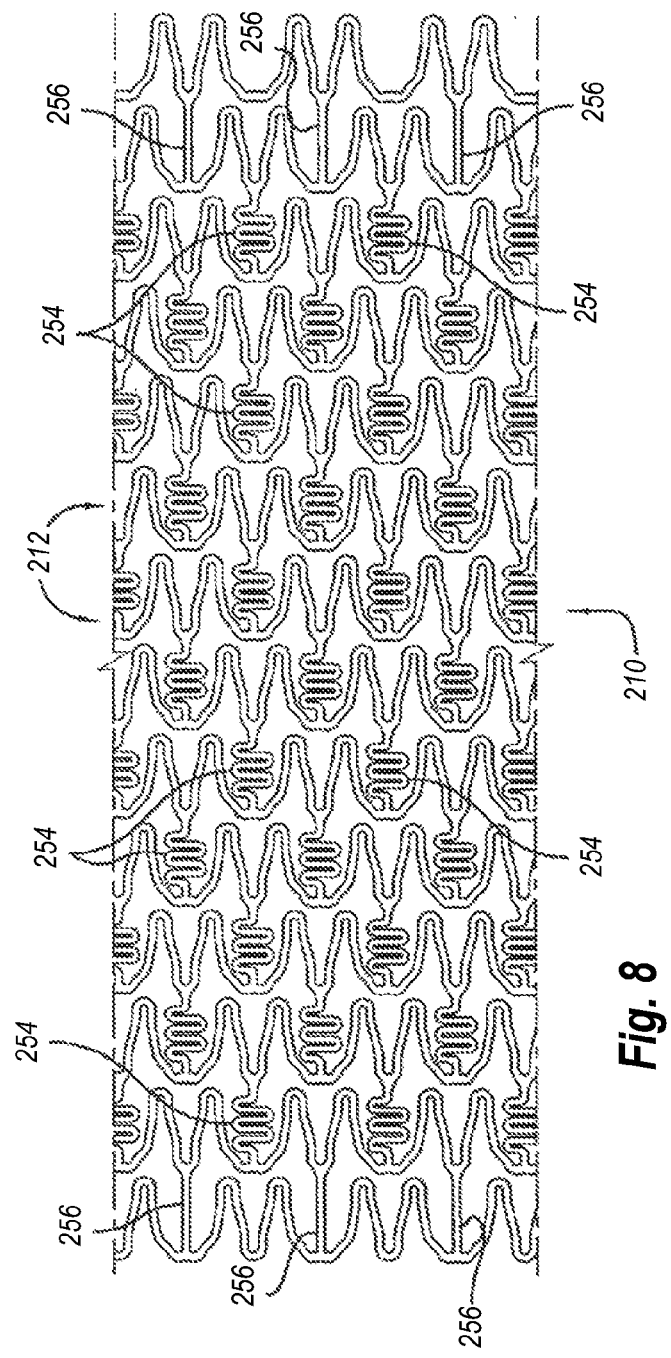
FIG. 8 is a plan view of a flattened stent embodying features of the invention, illustrating a combination of undulating links and straight links.

As shown in FIGS. 7 and 8, the stent 210 may be constructed with struts 252 formed from a Ni—Ti ternary alloy. In an example, struts 252a at the ends of the stent may be thicker than the struts 252b in the center of the stent 210 for purposes for increased radiopacity and to counter non-uniform expansion. In an embodiment, stent 210 may comprise a linear pseudo-elastic Ni—Ti ternary alloy, a superelastic Ni—Ti ternary alloy, and/or a shape memory Ni—Ti ternary alloy.

Figure 9:
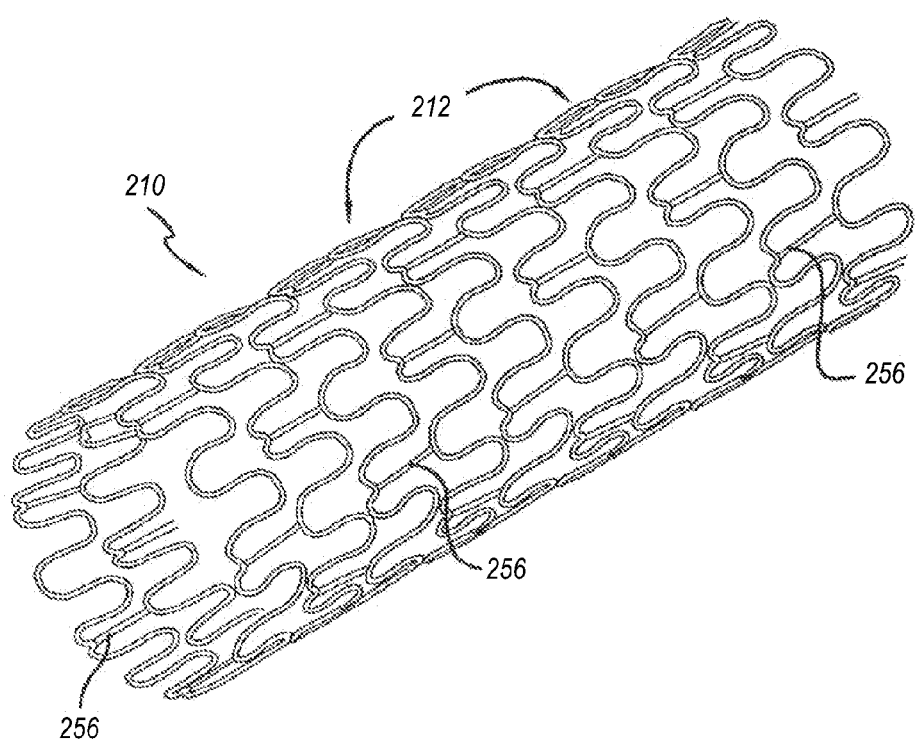
FIG. 9 is a perspective view of a stent embodying features of the invention, depicting cylindrical rings connected by straight links.

Referring to FIGS. 6, 8 and 9, each adjacent cylindrical ring 212 may be connected by at least one undulating link 254 or straight link 256. In an embodiment, the stent may include only straight links (FIG. 9), may include only undulating links (FIG. 6) or may include both undulating links and straight links (FIG. 8) to connect adjacent cylindrical rings. Both the straight links and the undulating links assist in preventing stent foreshortening. Further, the straight links may provide more stability and rigidity in a localized area, such as at the stent ends, such that it may be desirable to incorporate more straight links between the cylindrical rings at the stent ends, than in the center of the stent. An undulating link may be positioned substantially within the cylindrical plane 246, as defined by the cylindrical outer wall surface 248 and the cylindrical inner wall surface 250.

The stent 210 can be made in many ways. One method of making the stent is to cut a thin-walled tube of material to remove portions of the tubing in the desired pattern for the stent, leaving relatively untouched the portions of the metallic tubing that are to form the stent. Cutting of the tubing in the desired pattern may be by means of a machine-controlled laser. Other methods of forming the stent can be used, such as chemical etching; electric discharge machining; laser cutting a flat sheet and rolling it into a cylinder with a longitudinal weld; and the like. In addition, the stent and/or its struts may be formed from a wire or elongated fiber constructed from a Ni—Ti tyernary alloy material. The cross-section of such struts may be round, rectangular or any other suitable shape for constructing a stent.

C. Embolic Protection Devices

Figure 10:
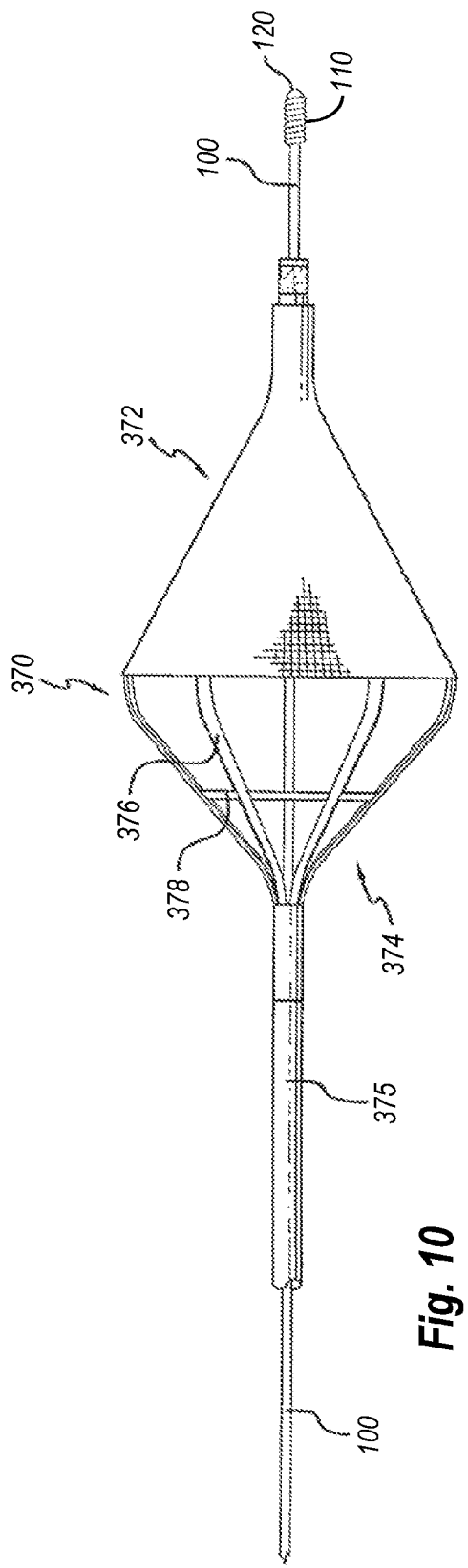
FIG. 10 depicts a longitudinal plan view of an embodiment of an expanded embolic protection device, including expandable struts.
Figure 11:
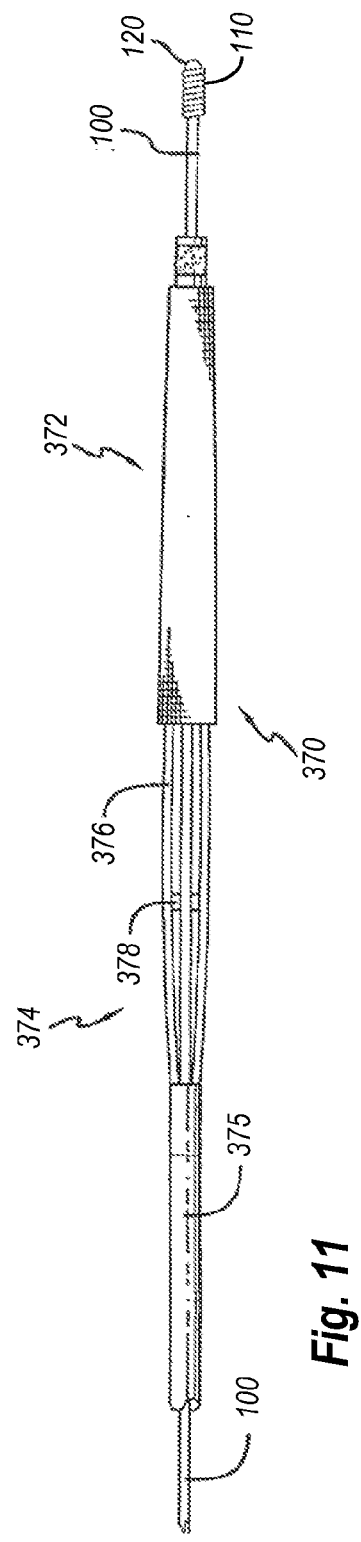
FIG. 11 depicts a longitudinal plan view of the embolic protection device of FIG. 10, wherein the device is collapsed for delivery into a corporal lumen.

Referring now to FIGS. 10 and 11, by way of example, the Ni—Ti ternary alloys described herein may be employed in fabrication of an embolic protection device 370. Such a device may include a filter assembly 372 and expandable strut assembly 374. The embolic protection device may further include an elongated tubular member 375, within which may be disposed a guide wire 100 for positioning the device within a body lumen. The embolic protection device may include a plurality of longitudinal struts 376 and transverse struts 378 that may be fabricated at least in part from a Ni—Ti ternary alloy according to the present disclosure. In addition, other components of the filter assembly may be formed from a Ni—Ti ternary alloy as heretofore described. As described above, guidewire 100 (including distal end 110 and/or 120) may include or be constructed from a Ni—Ti ternary alloy.

D. Graft Devices

Figure 12:
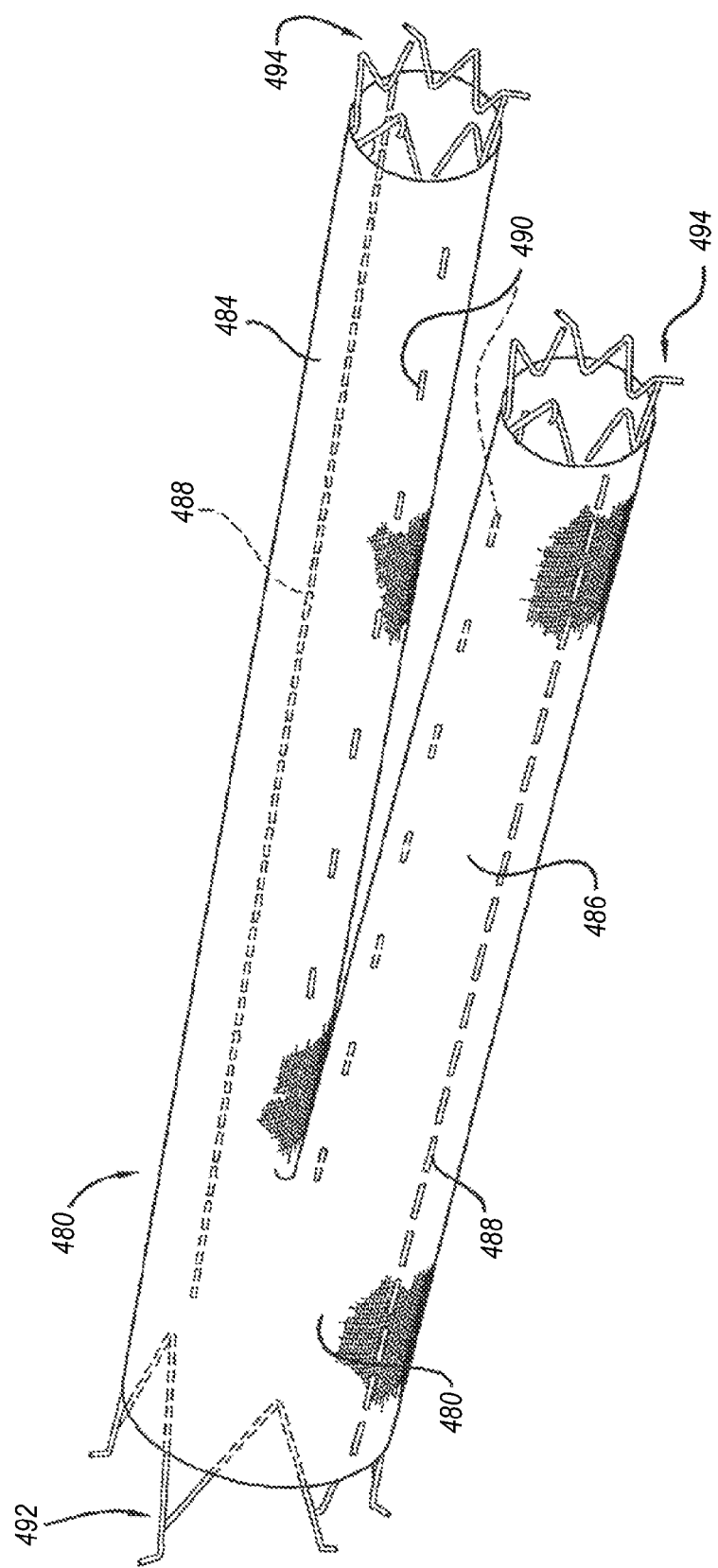
FIG. 12 depicts a perspective view of a graft assembly, including a plurality of attachment systems.

Referring now to FIG. 12, the Ni—Ti ternary alloys as described herein may be incorporated into a bifurcated graft 480 or a tubular graft (not shown). Such a graft may include a DACRON, TEFLON or other suitable flexible material having an upper body 482, a first leg 484 and a second leg 486, wherein the legs are joined to the upper body. Such a configuration forms a "Y" or "pants leg" configuration. A plurality of closely spaced markers 488 formed from a radiopaque material (e.g., which may be Ni—Ti—Ta) may be provided on the outside of the first and second legs. Similarly, wider spaced markers 490 may be provided on the inside of the legs of the bifurcated graft (or vice versa). Such markers may be formed from a Ni—Ti ternary alloy or other radiopaque materials, which may be sewn, glued or otherwise bonded to the graft.

In many such grafts 480, such as those used for repairing an abdominal aortic aneurysm, the upper body may include a first attachment system 492 positioned proximate to an upper opening of the graft. Tube grafts may contain a like attachment system at the lower opening of the graft. Similarly, bifurcated grafts may include smaller attachment systems 494 positioned at the end of the legs and proximate to the lower openings of the graft. As heretofore described regarding other intra-corporal medical devices, the attachment systems may be made of Ni—Ti ternary alloy in accordance with the present disclosure. Such stents and attachment systems may be of various configurations, such as, but not limited to, a ring and link design, a zigzag design, a coil design or a tubular mesh design.

While particular intra-corporal medical devices that may benefit from fabrication from the Ni—Ti ternary alloys described herein have been illustrated and described, it will be apparent to those skilled in the art that other medical devices (e.g., closure elements) may be formed from such alloys. Likewise, the invention is not limited to any particular method of forming the under lying medical device structure.

III. Methods for Fabricating a Medical Device

In an embodiment, a method for fabricating a medical implant or medical device is disclosed. The method includes (1) providing a nickel-titanium (Ni—Ti) alloy ingot that comprises nickel (Ni), titanium (Ti), and a ternary alloying element selected from the group consisting of tantalum (Ta), hafnium (Hf), vanadium (V), zirconium (Zr), and combinations thereof. The method further includes (2) fabricating one or more components of the medical implant or medical device from the Ni—Ti alloy ingot to yield a structure in which the first phase and the second phase are arranged in a structure including elongate bands of a Ni—Ti rich phase and elongate bands containing a eutectic mixture of both phases. The one or more components of the medical implant or medical device fabricated from the Ni—Ti alloy have one or more of an elastic modulus in an austenitic phase of greater than about 85 GPa, an elastic modulus in a martensitic phase of greater than about 42 GPa, or a martensite transformation temperature of less than about −5° C.

In one embodiment, the ternary alloying element is included in an amount sufficient to yield an alloy having a two phase structure showing primary dendrites of a first phase rich in Ni—Ti and a eutectic mixture of the first phase and a second phase rich in the ternary alloying element. The dual phase Ni—Ti ternary alloy system includes two ductile phases having widely different mechanical properties. Cast ingots of the Ni—Ti ternary alloy may contain dendrites of the Ni—Ti rich first phase 502 surrounded by a eutectic mixture of both phases 504 (FIG. 13A). Upon working down the cast material 500 to produce a guide wire or other intra-corporal body structure (e.g., by one or more of drawing, stamping, rolling, flattening, swaging, or other suitable working techniques), the dendrites 502 become elongated, resulting in a microstructure which is not completely homogenous and which includes small second phase particles that are rich in the ternary alloying element surrounded by the Ni—Ti rich first phase. In one embodiment (FIG. 13B), the structure 510 includes thin elongate bands 512 of the first Ni—Ti rich phase surrounded by bands comprised of both phases 514. Such a structure may be directional (e.g., in the direction of the rolling, drawing, etc.).

In one embodiment, the medical device or one or more portions of a medical device can be fabricated from a billet or ingot of the Ni—Ti ternary alloy using at least one of drawing or grinding. Suitable examples of cold working procedures that can be used to cold work either selected sections of the medical device or the whole medical device include, but are not limited to, drawing, high force flattening, stamping, rolling, calendaring, and combinations thereof. If a linear pseudo-elastic structure is desired, the cold working may be followed by minimal or no heat treatment. If a superelastic and/or shape memory structure is desired, the cold work may be followed by heat treatment sufficient to relieve the stress-induced martensite state in the cold worked alloy.

In one embodiment, the cold-worked section(s) may include about 20% to about 90% cold work, about 30% to about 65% cold work, about 40% cold work to about 50% cold work, or about 45% cold work. The cold work imparts a martensitic phase having a linear pseudo-elastic microstructure with linear pseudo-elastic behavior without a phase transformation or onset of stress-induced martensite. In one embodiment, the martensitic phase is enhanced and/or stabilized by the cold working.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A medical device, comprising:
a body;
at least a portion of the body being fabricated from a nickel-titanium (Ni—Ti) alloy comprising nickel (Ni), titanium (Ti), and a ternary alloying element selected from the group consisting of tantalum (Ta), hafnium (Hf), vanadium (V), zirconium (Zr), and combinations thereof,
wherein the ternary alloying element is present in the Ni—Ti alloy in an amount ranging from about 4 atomic % (at %) to about 30 at %,
wherein the Ni—Ti alloy has a first phase rich in Ni—Ti and a second phase rich in the ternary alloying element, and one or more of: an elastic modulus in an austenite phase of greater than about 85 GPa, an elastic modulus in a martensite phase of greater than about 42 GPa, or a martensite transformation (Ms) temperature of less than about −5° C.; and
wherein the first phase and the second phase are arranged in a lamellar structure including elongate bands of the first phase surrounded by elongate bands of the second phase.

2. The medical device of claim 1, wherein the body comprises at least a portion of one or more of a guide wire device, an implantable vascular endoprosthesis, at least a portion of a rapid exchange balloon catheter, at least a portion of a rapid exchange stent delivery catheter, or an embolic protection filter.

3. The medical device of claim 2, wherein the implantable vascular endoprosthesis comprises a self-expanding stent.

4. The medical device of claim 1, wherein the Ni—Ti alloy exhibits superelastic behavior.

5. The medical device of claim 1, wherein the Ni—Ti alloy exhibits linear pseudo-elastic behavior without a phase transformation or onset of stress-induced martensite.

6. The medical device of claim 1, wherein the Ni—Ti alloy is a shape memory alloy.

7. The medical device of claim 1, wherein the Ni—Ti alloy is a ternary alloy consisting of Ni, Ti, and Ta.

8. The medical device of claim 7, wherein the Ni—Ti alloy comprises about 35 at % to about 55 at % Ni, about 35 at % to about 55 at % Ti, and about 4 at % to about 30 at % of Ta.

9. A method for fabricating a medical implant or medical device, the method comprising:
- providing a nickel-titanium (Ni—Ti) alloy ingot that comprises nickel (Ni), titanium (Ti), and a ternary alloying element selected from the group consisting of tantalum (Ta), hafnium (Hf), vanadium (V), zirconium (Zr), and combinations thereof, wherein the ingot has a two phase structure showing primary dendrites of a first phase rich in Ni—Ti and secondary dendrites of a second phase rich in the ternary alloying element; and
- fabricating one or more components of the medical implant or medical device from the Ni—Ti alloy ingot to yield a structure in which the first phase and the second phase are arranged in a lamellar structure including elongate bands of the first phase surrounded by elongate bands of the second phase,
- wherein the one or more components of the medical implant or medical device fabricated from the Ni—Ti alloy have one or more of an elastic modulus in an austenitic phase of greater than about 85 GPa, an elastic modulus in a martensitic phase of greater than about 42 GPa, or a martensite transformation temperature of less than about −5° C.

10. The method of claim 9, wherein the one or more components of the medical implant or medical device fabricated from the Ni—Ti alloy exhibit one or more of superelastic behavior, linear pseudo-elastic behavior without a phase transformation or onset of stress-induced martensite, or shape memory.

11. The method of claim 9, wherein the fabricating includes at least one of drawing, stamping, laser-cutting, or grinding.

12. The method of claim 9, wherein the fabricating includes cold working Ni—Ti alloy without subsequent heat treatment or with limited heat treatment to yield one or more components of the medical implant or medical device exhibiting linear pseudo-elastic behavior without a phase transformation or onset of stress-induced martensite, wherein the limited heat treatment is of a duration sufficient to preserve linear pseudo-elastic behavior and of a duration insufficient to induce superelastic and/or shape memory behavior.

13. The method of claim 9, wherein the fabricating includes hot-working and/or heat-treating the Ni—Ti alloy to yield one or more components of the medical implant or medical device exhibiting superelastic behavior and/or shape memory.

14. The method of claim 9, wherein the one or more components of the medical implant or medical device have one or more of an elastic modulus of about 50 gigapascals (GPa) to about 100 GPa in the martensitic phase or an elastic modulus of about 85 gigapascals (GPa) to about 150 GPa in the austenitic phase.

15. The method of claim 9, wherein the Ni—Ti alloy is a ternary alloy consisting of Ni, Ti, and Ta.

16. The method of claim 9, wherein the medical implant or medical device comprises at least a portion of one or more of a guide wire device, an implantable vascular endoprosthesis, at least a portion of a rapid exchange balloon catheter, at least a portion of a rapid exchange stent delivery catheter, or an embolic protection filter.

* * * * *